United States Patent [19]
Hofrichter et al.

[11] Patent Number: 5,429,816
[45] Date of Patent: Jul. 4, 1995

[54] ANTIPERSPIRANT GEL STICK COMPOSITIONS

[75] Inventors: Brian D. Hofrichter, Hunt Valley, Md.; John M. Gardlik; Philip A. Sawin, both of Cincinnati, Ohio; John P. Luebbe, Lawrenceburg, Ind.; Barton J. Bradbury, West Chester, Ohio

[73] Assignee: Procter & Gamble, Cincinnati, Ohio

[21] Appl. No.: 85,424

[22] Filed: Jun. 30, 1993

Related U.S. Application Data

[63] Continuation-in-part of Ser. No. 881,934, May 12, 1992, abandoned.

[51] Int. Cl.6 .......................... A61K 7/32; A61K 7/34; A61K 7/38
[52] U.S. Cl. ................. 424/66; 424/DIG. 5; 424/67; 424/68; 514/944
[58] Field of Search ............ 424/65, 66, DIG. 5

[56] References Cited

U.S. PATENT DOCUMENTS

| | | | |
|---|---|---|---|
| 2,890,987 | 6/1959 | Hilfer | 167/90 |
| 2,900,306 | 8/1959 | Slater | 167/90 |
| 3,255,082 | 6/1966 | Barton | 167/90 |
| 3,792,068 | 2/1974 | Luedders | 260/429.3 |
| 3,887,692 | 6/1975 | Gilman | 423/462 |
| 3,903,258 | 9/1975 | Siegal | 424/66 |
| 3,904,741 | 9/1975 | Jones et al. | 423/462 |
| 3,969,087 | 7/1976 | Saito et al. | 44/7 C |
| 3,970,748 | 7/1976 | Mecca | 424/68 |
| 3,979,510 | 9/1976 | Rubino | 424/47 |
| 3,981,896 | 9/1976 | Pauling | 260/429 |
| 4,017,599 | 4/1977 | Rubino | 424/47 |
| 4,049,792 | 9/1977 | Elsnau | 424/66 |
| 4,053,581 | 10/1977 | Pader et al. | 424/68 |
| 4,126,679 | 11/1978 | Davy et al. | 424/66 |
| 4,137,306 | 1/1979 | Rubino | 424/68 |

(List continued on next page.)

FOREIGN PATENT DOCUMENTS

| | | | |
|---|---|---|---|
| 1164347 | 3/1984 | Canada | A61K 7/32 |
| 1266003 | 4/1986 | Canada | A61K 7/32 |
| 2057081 | 12/1991 | Canada | A61K 7/38 |
| 117070 | 8/1984 | European Pat. Off. | A61K 7/32 |
| 0286522 | 1/1988 | European Pat. Off. | C07D 493/04 |
| 0373499 | 6/1988 | European Pat. Off. | A61K 7/38 |
| 0295070 | 12/1988 | European Pat. Off. | A61K 7/32 |
| 0295071 | 12/1988 | European Pat. Off. | A61K 7/32 |
| 373424 | 11/1989 | European Pat. Off. | A61K 7/02 |
| 0396137 | 11/1990 | European Pat. Off. | A61K 7/32 |
| 0448278 | 9/1991 | European Pat. Off. | A61K 7/38 |
| 61-206450 | 9/1986 | Japan | A61L 9/01 |
| 62-265393 | 11/1987 | Japan | C10L 3/00 |
| 1020286 | 1/1989 | Japan | C09K 3/00 |
| 64-62377 | 3/1989 | Japan | |
| 1-207223 | 8/1989 | Japan | A61K 7/02 |
| 2-180805 | 7/1990 | Japan | A61K 7/00 |
| 2-264707 | 10/1990 | Japan | |
| 3-170415 | 7/1991 | Japan | A61K 7/32 |
| 4208202 | 7/1992 | Japan | A01N 25/18 |
| 1485694 | 9/1977 | United Kingdom | B01F 17/28 |
| 2253347 | 9/1992 | United Kingdom | A61K 7/32 |

OTHER PUBLICATIONS

Ser. No. 08/053,618 to Sawin & Luebbe on Apr. 25, 1993 (abandoned Jul. 25, 1993).

Ser. No. 07/530,671 to Cedeno et al. on May 30, 1990 (abandoned Jul. 2, 1991).

(List continued on next page.)

Primary Examiner—Dale R. Ore
Attorney, Agent, or Firm—Leonard W. Lewis; John M. Howell; Michael E. Hilton

[57] ABSTRACT

An antiperspirant gel stick composition incorporating a gelling agent, including a primary gellant selected from the group consisting of 12-hydroxystearic acid, esters of 12-hydroxystearic acid, amides of 12-hydroxystearic acid, and mixtures thereof and a secondary gellant selected from the group consisting of n-acyl amino acid amide derivatives. The antiperspirant gel stick compositions further incorporate a liquid base material including a non-polar, volatile oil and a relatively polar, non-volatile co-solvent. The combination of the gelling agent and the co-solvent permit the utilization of relatively high levels of a non-polar volatile oils which provide a dry feel.

24 Claims, No Drawings

U.S. PATENT DOCUMENTS

| | | | |
|---|---|---|---|
| 4,147,766 | 4/1979 | Kozischek | 424/14 |
| 4,151,272 | 4/1979 | Geary | 424/68 |
| 4,154,816 | 5/1979 | Roehl et al. | 424/68 |
| 4,202,879 | 5/1980 | Shelton | 424/66 |
| 4,226,889 | 10/1980 | Yuhas | 424/59 |
| 4,371,645 | 2/1983 | Mahaffey, Jr. | 524/108 |
| 4,425,328 | 1/1984 | Nabial | 424/68 |
| 4,429,140 | 1/1984 | Murai et al. | 549/370 |
| 4,518,582 | 5/1985 | Schamper et al. | 424/66 |
| 4,719,102 | 1/1988 | Randhawa et al. | 424/66 |
| 4,722,835 | 2/1988 | Schamper et al. | 424/66 |
| 4,725,430 | 2/1988 | Schamper et al. | 424/66 |
| 4,781,917 | 11/1988 | Luebbe et al. | 424/65 |
| 4,816,261 | 3/1989 | Luebbe et al. | 424/65 |
| 4,822,602 | 4/1989 | Sabatelli | 424/65 |
| 4,822,603 | 4/1989 | Farris et al. | 424/66 |
| 4,919,934 | 4/1990 | Deckner et al. | 424/402 |
| 4,944,937 | 7/1990 | McCall | 424/65 |
| 4,948,578 | 8/1990 | Burger et al. | 424/68 |
| 4,985,238 | 1/1991 | Tanner et al. | 424/66 |
| 5,019,375 | 5/1991 | Tanner et al. | 424/66 |
| 5,106,999 | 4/1992 | Gardlik et al. | 549/364 |
| 5,200,174 | 4/1993 | Gardlik et al. | 424/66 |

OTHER PUBLICATIONS

Ser. No. 07/370,559 to Smith & Ward on Jun. 23, 1989 (abandoned Jul. 30, 1990).

Balsam and Sagarin, Cosmetics, Science, and Technology, vol. 1, 27–104, 1972.

Geria, "Formulation of Stick Antiperspirants and Deodorants", *Cosmetics and Toiletries,* 99:55–60 (1984).

*Gels and Sticks Formulary,* 99 Cosmetics & Toiletries 82–87, 1984.

Todd et al., "Volatile Silicone Fluids for Cosmetics", *Cosmetics and Toiletries,* 91:29–32 (1976).

Chemical Abstracts, vol. 85, No. 2, No. 85:10310 (1976).

C. D. Vaughn, "Solubility Effects in Product, Package, Penetration and Preservation" 103 *Cosmetics and Toiletries* 47–69, Oct., 1988.

Plechner, *Antiperspirants and Deodorants,* 2 Cosmetics, Science and Technology, Balsam and Sagarin, 374–400, 1972.

Homma, Masao, "Oil Gelating Agent Using Amino Acids", (Modern Chemistry), 54–59, Aug., 1987 (translation).

C. D. Vaughan, "Using Solubility Parameters in Cosmetic Formulation", 36 *J. Soc. Cosmetic Chemists* 319–333, Sep./Oct., 1985.

ANTIPERSPIRANT GEL STICK COMPOSITIONS

This is a continuation-in-part of application Ser. No. 881,934, filed on May 12, 1992 now abandoned.

FIELD OF THE INVENTION

The present invention relates to antiperspirant stick compositions useful in preventing perspiration and body odors; and more particularly, to such antiperspirant compositions which are in the form of a gel stick.

BACKGROUND OF THE INVENTION

Personal hygienic habits typically include a means for reducing human body odors. These habits include routine bathing or washing of the body, particularly the axilla, and treating the axilla with compositions to retard odor formation, such as antiperspirant compositions.

Antiperspirants are well known in the art, and generally include an astringent material in a suitable carrier. Astringent materials typically used in antiperspirants are metal salts, particularly aluminum and zinc metal complexes. Exemplary metal salts are disclosed in Plechner, *Antiperspirants and Deodorants*, 2 Cosmetics, Science and Technology, Balsam and Sagarin, 374-400, 1972; herein incorporated by reference.

Antiperspirant compositions can take a number of different forms, each dependent on the ingredients used in addition to the above mentioned astringent metallic salts. The forms include lotions, solid sticks, and creams; the most popular being solid sticks. Gel sticks are one class of such solid stick antiperspirant compositions.

Antiperspirant gel stick compositions are known in the art. These sticks contain a liquid material and gelling agents. The liquid materials typically are water, lower monohydric alcohols, polyhydric alcohols, and mixtures thereof. The gelling agents most often used include fatty acid soaps, and dibenzylidine monosorbitol acetals (hereinafter DBS). See the following exemplary patents related to antiperspirant stick compositions utilizing soap gels: U.S. Pat. Nos. 3,255,082, Barton, issued Jun. 7, 1966; 4,137,306, Rubino, issued Jan. 30, 1979; 4,944,937, McCall, issued Jul. 31, 1990. See the following exemplary patents related to antiperspirant stick compositions utilizing DBS gels: U.S. Pat. Nos. 4,154,816, Roehl et al, issued May 15, 1979; 4,518,582, Schamper et al, issued May 21, 1985; 4,719,102, Randhawa et al, issued Jan. 12, 1988; 4,722,835, Schamper et al, issued Feb. 2, 1988; 4,725,430, Schamper et al, issued Feb. 16, 1988; 4,781,917, Luebbe et al, issued Nov. 1, 1988; 4,816,261, Luebbe et al, issued Mar. 28, 1989; 4,822,602, Sabetelli, issued Apr. 18, 1989; and 5,106,999, Gardlik et al, issued Apr. 21, 1992.

One significant disadvantage of typical antiperspirant gel stick compositions is a tendency to experience problems associated with interaction between the gelling agent and the acidic antiperspirant actives. For example, the antiperspirant active tends to degrade the acetal portion of the DBS gellant. In fact, improving the stability of DBS gels has been the object of many of the DBS patents cited above. This interaction between the gelling agent and the antiperspirant active can result in reduced efficacy of the actives, poor gel formation, and lower gel stability over time of any gel which is formed. The interaction may also cause processing difficulties at the temperatures and holding times typically encountered during manufacturing.

Furthermore, such antiperspirant gel stick compositions may have additional disadvantages. For example, DBS must be dissolved in a polar solvent. Polar solvents, however, tend to contribute to undesirable stick characteristics such as wet, cold and sticky feel on the skin, shrinkage and containment problems due to high volatility, and skin irritation.

Other gelling agents have been utilized for gelling various non-antiperspirant compositions; such as fuels, motor oils, paints, edible oils, and cosmetics. For example, information regarding the use of n-acyl amino acids as gellants are found in the following references: U.S. Pat. No. 3,969,087 issued on Jul. 13, 1976 to Saito et al.; Japanese Patent Application 1-207223, published Aug. 21, 1989; Japanese Patent Application 1-207223 which published Aug. 21, 1989; and Japanese Patent Application 2-180805 which published Jul. 13, 1988.

Furthermore, information regarding the use of 12-hydroxystearic acid as a gelling agent for non-antiperspirant compositions is disclosed in the following references: Japanese Patent Application 2-180805, cited supra; and Japanese Patent Application 2-264707, published Oct. 31, 1990.

As discussed herein, none of these references provide an antiperspirant gel stick composition having the unique combination of desirable characteristics of the composition of the present invention. For example, the combination of gellants which comprise the gelling agent are stable in the presence of the antiperspirant active during manufacturing; i.e., at the required process temperatures for typical process durations. Additionally, the preferred antiperspirant gel stick composition has good aesthetics due to the inclusion of a non-polar, volatile oil effective for improving skin feel. Incorporation of an effective amount of the non-polar, volatile oil is made possible through the inclusion of a small amount of a relatively polar, non-volatile co-solvent.

SUMMARY OF THE INVENTION

The present invention is an antiperspirant gel stick composition comprising:
 a. an antiperspirant active;
 b. a gelling agent including a primary gellant selected from the group consisting of 12-hydroxystearic acid, esters of 12-hydroxystearic acid, amides of 12-hydroxystearic acid, and mixtures thereof, and a secondary gellant selected from the group consisting; of n-acyl amino acid amide derivatives; and
 c. a liquid base material; preferably including a non-polar, volatile oil, and a relatively polar, non-volatile co-solvent, the relatively polar, non-volatile co-solvent being soluble in the non-polar, volatile oil and being capable of solublizing the primary gellant or the secondary gellant.

DETAILED DESCRIPTION OF THE INVENTION

Antiperspirant gel stick compositions of the present invention include the ingredients discussed below. Although the term "stick" as utilized herein includes semi-solid forms (i.e., preferably having a viscosity of at least about 1,000,000 centipoise at 25° C.), solid forms (i.e., preferably having an average penetration value within a given production batch from about 3 to about 25 mm over a period of 5 seconds as measured utilizing American Society for Testing Materials (ASTM) Method D-5, with a penetration cone (Model H1312; sold by Humbolt Manufacturing Company) weighing 2.0 g (making the total mass 50 g and a Sommer & Runge Model PNR10 Penetrometer) are preferred.

A. Gelling Agent:

The "gelling agent" as used herein is a mixture of a primary gellant and a secondary gellant; both discussed hereinafter. The primary gellant is selected from the group consisting of 12-hydroxystearic acid, esters of 12-hydroxystearic acid, amides of 12-hydroxystearic acid and mixtures thereof. The secondary gellant is selected from the group consisting of n-acyl amino acid derivatives. The level of the gelling agent within the composition is typically from about 1% to about 15%; preferably, from about 3% to about 12%; more preferably, from about 5% to about 10%. The primary gellant-:secondary gellant ratio is typically between about 1:2 and about 20:1; preferably, from about 1:1 to about 10:1; more preferably, from about 2:1 to about 7:1; and even more preferably, from about 3:1 to about 5:1. The primary gellant:secondary gellant ratio appears to be more critical when the level of polar, non-volatile liquid within the liquid base material (discussed hereinafter) in the composition is relatively low; e.g., below about 25%.

This gelling agent offers significant benefits when used in an antiperspirant gel stick. The gelling agent of the present invention exhibits unexpected benefits, e.g., decreased residue upon application to the skin, increased hardness and better aesthetics, relative to a similar composition having either of the two gellants alone. In fact, these gellants in combination are more effective than either alone so that the overall level of gelling agent within the composition can be reduced while maintaining such desirable stick characteristics.

Moreover, when these gellants are used together as the galling agent of the present invention, degradation of the gelling agent by the acidic antiperspirant active during manufacturing is unexpectedly significantly reduced; i.e., as compared to each gellant alone. To further reduce degredation, a heated solution of the gelling agent and the liquid base material preferably remains in solution such that the antiperspirant active can be substantially uniformly mixed therein at a temperature less than about 120° C.; more preferably, less than about 105° C.; more preferably, less than about 95° C.; and most preferably, less than about 80° C. (hereinafter, the "mixing temperature"). This reduced mixing temperature is made possible partly because the primary gellant, once molten, is an unexpectedly good co-solvent for the secondary gellant, thereby facilitating their dissolution at a lower temperature. Additional methods of reducing the mixing temperature or otherwise enabling a reduction of the interaction of the acidic antiperspirant active with other components, e.g., the gelling agent, is discussed hereinafter. Since lower mixing temperatures can be utilized, the gelling agent is more compatible with additional gel stick components which have lower boiling points, such as perfumes.

1. Primary Gellant

The primary gellant of the gelling agent of the present invention is selected from the group consisting of 12-hydroxystearic acid, esters of 12-hydroxystearic acid, amides of 12-hydroxystearic acid and mixtures thereof. Thus, the primary gellant corresponds to the following formula:

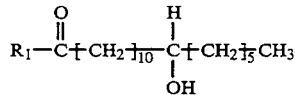

wherein $R_1$ is $OR_2$ or $NR_2R_3$; and $R_2$ and $R_3$ are hydrogen, or an alkyl, aryl, or arylalkyl radical which is branched linear or cyclic and has from about 1 to about 22 carbon atoms; preferably, from about 1 to about 18 carbon atoms. $R_2$ and $R_3$ may be either the same or different; however, at least one is preferably a hydrogen atom.

The primary gellant is preferably selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, and mixtures thereof, even more preferably, 12-hydroxystearic acid, isopropyl amide of 12-hydroxystearic acid, and mixtures thereof.

2. Secondary Gellant

With regard to the secondary gellant of the gelling agent of the present invention, n-acyl amino acid derivatives include n-acyl amino acid amides and n-acyl amino acid esters prepared from glutamic acid, lysine, glutamine, aspartic acid and mixtures thereof. Particularly preferred are n-acyl glutamic acid amides and n-acyl glutamic acid esters corresponding to the following formula:

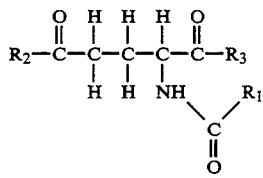

wherein $R_1$ is an alkyl, aryl, arylalkyl radical (branched, linear or cyclic), having from about 1 to about 26 carbon atoms; preferably, from about 6 to about 22 carbon atoms; more preferably, from about 12 to about 18 carbon atoms. $R_2$ and $R_3$ are the same or different—preferably the same—alkyl, aryl, arylalkyl ester radical or amide radical, in which the alkyl, aryl, arylalkyl moeity (branched, linear or cyclic) has from about 1 to about 26 carbon atoms; preferably, from about 2 to about 20 carbon atoms.

Preferably the n-acyl amino acid derivatives are selected from the group consisting of N-lauroyl-glutamic acid diethyl amide, N-lauroyl-glutamic acid dibutyl amide, N-lauroyl-glutamic acid dihexyl amide, N-lauroyl-glutamic acid dioctyl amide, N-lauroyl-glutamic acid didecyl amide, N-lauroyl-glutamic acid didodecyl amide, N-lauroyl-glutamic acid ditetradecyl amide, N-lauroyl-glutamic acid dihexadecyl amide, N-lauroyl-glutamic acid distearyl amide, N-stearoyl-glutamic acid dibutyl amide, N-stearoyl-glutamic acid dihexyl amide, N-stearoyl-glutamic acid diheptyl amide, N-stearoyl-glutamic acid dioctyl amide, N-stearoyl-glutamic acid didecyl amide, N-stearoyl-glutamic acid didodecyl amide, N-stearoyl-glutamic acid ditetradecyl amide, N-stearoyl-glutamic acid dihexadecyl amide, N-stearoyl-glutamic acid distearyl amide and mixtures thereof; more preferred, is n-lauroyl-glutamic acid dibutyl amide, n-stearyl-glutamic acid dihexyl amide, and mixtures thereof.

B. Liquid Base Material

The liquid base matrix of antiperspirant stick compositions of the present invention is formed by combining the gelling agent with a liquid base material. As o used herein, the term "liquid" refers to materials which are liquids at ambient conditions and the term "liquid base material" includes all liquids within the composition. It is important that the liquid base material be of a type, and used at a level sufficient to solubilize the gelling agent when heated, to permit substantially uniform mixing of the antiperspirant active into the heated solution at the mixing temperature, and form a stick when cooled to ambient temperature. The liquid base material must be compatible with the gelling agent so that the mixture of the two remains homogeneous and does not phase separate during manufacturing and so that the finished product remains homogeneous and does not phase separate at ambient conditions over the normal shelf-life which may be upwards of one year. Furthermore, the liquid base materials are typically selected to provide aesthetic benefits, such as emolliency, low tack or minimized visible residue, without significant interference with the effectiveness of the antiperspirant active component. Lastly, the particular liquid base material should be safe for application to human skin.

The liquid base materials include emollients which have a solubility parameter from about 5 to about 11. It is preferable that, in aggregate, the average solubility parameter of the liquid base material be from about 6 to about 10. Hence, a mixture of emollients may be used as the liquid base material herein, each having a solubility parameter in the range of from about 5 to about 11, such that the average solubility parameter of the mixture is from about 6 to about 10. Solubility parameters are common to the art of antiperspirant stick formulation and the means to determine them are disclosed by C. D. Vaughan, "Solubility Effects in Product, Package, Penetration and Preservation" 103 Cosmetics and Toiletries 47–69, October, 1988; and C. D. Vaughan, "Using Solubility Parameters in Cosmetics Formulation", 36 J Soc. Cosmetic Chemists 319–333, September/October, 1985.

The liquid base material of the present invention is preferably used at levels from about 10% to about 95%; and more preferably from about 45% to about 80%. The liquid base material preferably includes a volatile, non-polar, oil and a non-volatile, relatively polar co-solvent; each discussed more fully hereinafter. The term "non-volatile" as used herein refers to materials which exhibit a vapor pressure of no more than about 0.2 mm Hg at 25° C. at one atmosphere and/or to materials which have a boiling point at one atmosphere of at least about 300° C. The term "volatile" as used herein refers to all materials which are not "non-volatile" as previously defined herein. The phrase "relatively polar" as used herein means more polar than another material in terms of solubility parameter; i.e., the higher the solubility parameter the more polar the liquid. The term "non-polar" typically means that the emollient has a solubility parameter below about 6.5.

1. Non-polar, Volatile Oil

The non-polar, volatile oil tends to impart highly desirable aesthetic properties to the gel stick. Consequently, the non-polar, volatile oils are preferably utilized at a fairly high level. Such non-polar, volatile oils are preferably used at levels from about 10% to about 70%; more preferably, from about 25% to about 60%; more preferably from about 40% to about 60%.

Non-polar, volatile oils particularly useful in the present invention are selected from the group consisting of silicone oils; hydrocarbons; and mixtures thereof. Such non-polar, volatile oils are disclosed, for example, in Cosmetics, Science, and Technology, Vol. 1, 27–104 edited by Balsam and Sagarin, 1972. The non-polar, volatile oils useful in the present invention may be either saturated or unsaturated, have an aliphatic character and be straight or branched chained or contain alicyclic or aromatic rings. Examples of preferred non-polar, volatile hydrocarbons include isodecane (such as Permethyl-99A which is available from Presperse Inc.) and the $C_7$-$C_8$ through $C_{12}$-$C_{15}$ isoparaffins (such as the Isopar Series available from Exxon Chemicals).

Non-polar, volatile silicone oils are highly preferred as the non-polar, volatile oil in the liquid base material, since they endow the antiperspirant stick composition with highly desirable aesthetics. Non-polar, volatile liquid silicone oils are disclosed in U.S. Pat. No. 4,781,917 issued to Luebbe et al. on Nov. 1, 1988. Additionally, a description of various volatile silicones materials is found in Todd et al., "Volatile Silicone Fluids for Cosmetics", Cosmetics and Toiletries, 91:27–32 (1976). Particularly preferred volatile silicone oils are selected from the group consisting of cyclic volatile silicones corresponding to the formula:

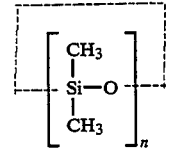

wherein n is from about 3 to about 7; and linear volatile silicones corresponding to the formula:

wherein m is from about 1 to about 7. Linear volatile silicones generally have a viscosity of less than about 5 centistokes at 25° C., whereas the cyclic silicones have viscosities of less than about 10 centistokes at 25° C. Highly preferred examples of volatile silicone oils include cyclomethicones of varying viscosities, e.g., Dow Corning 200, Dow Corning 244, Dow Corning 245, Dow Corning 344, and Dow Corning 345, (commercially available from Dow Corning Corp.); SF-1204 and SF-1202 Silicone Fluids (commercially available from G.E. Silicones), GE 7207 and 7158 (commercially available from General Electric Co.); and SWS-03314 (commercially available from SWS Silicones Corp.).

2. Relatively Polar, Non-volatile Co-solvent

The relatively polar co-solvent aids in the utilization of reduced processing temperatures by solubilizing at least one of the gellants and being soluble in the non-polar, volatile oil when subjected to reduced processing temperatures. The non-volatile co-solvent is "relatively polar" as compared to the non-polar, volatile oil discussed above. Therefore, the non-volatile co-solvent is more polar (i.e., has a higher solubility parameter) than at least one of the non-polar, volatile oils.

In addition to enabling reduced processing temperatures, the co-solvent enables the inclusion of greater amounts of the non-polar, volatile oil. This is advantageous because, as discussed above, the non-polar, volatile oil provides significant cosmetic benefits. The quantity of relatively polar, non-volatile co-solvent, however, is preferably kept to a minimum because it tends to adversely affect product cosmetics. Thus, the relatively polar, non-volatile co-solvent is preferably included at levels from about 5% to about 60%; more preferably from about 5% to about 25%; and most preferably from about 7% to about 20%.

Relatively polar, non-volatile liquids potentially useful as the co-solvent in the present invention are disclosed, for example, in Cosmetics, Science, and Technology, Vol. 1, 27–104 edited by Balsam and Sagarin, 1972; U.S. Pat. Nos. 4,202,879 issued to Shelton on May 13, 1980; and 4,816,261 issued to Luebbe et al. on Mar. 28, 1989. Relatively polar, non-volatile co-solvents useful in the present invention are preferably selected from the group consisting of silicone oils; hydrocarbon oils; fatty alcohols; fatty acids; esters of mono and dibasic carboxylic acids with mono and polyhydric alcohols; polyoxyethylenes; polyoxypropylenes; mixtures of polyoxyethylene and polyoxypropylene ethers of fatty alcohols; and mixtures thereof. The relatively polar, non-volatile co-solvents useful in the present invention may be either saturated or unsaturated, have an aliphatic character and be straight or branched chained or contain alicyclic or aromatic rings.

More preferably, the relatively polar, non-volatile liquid co-solvent are selected from the group consisting of fatty alcohols having from about 12–26 carbon atoms; fatty acids having from about 12–26 carbon atoms; esters of monobasic carboxylic acids and alcohols having from about 14–30 carbon atoms; esters of dibasic carboxylic acids and alcohols having from about 10–30 carbon atoms; esters of polyhydric alcohols and carboxylic acids having from about 5–26 carbon atoms; ethoxylated, propoxylated, and mixtures of ethoxylated and propoxylated ethers of fatty alcohols with from about 12–26 carbon atoms and a degree of ethoxylation and propoxylation of below about 50; and mixtures thereof.

More preferred are propoxylated ethers of $C_{14}$–$C_{18}$ fatty alcohols having a degree of propoxylation below about 50, esters of $C_2$–$C_8$ alcohols and $C_{12}$–$C_{26}$ carboxylic acids (e.g. ethyl myristate, isopropyl palmitate), esters of $C_{12}$–$C_{26}$ alcohols and benzoic acid (e.g. Finsolv TN supplied by Finetex), diesters of $C_2$–$C_8$ alcohols and adipic, sebacic, and phthalic acids (e.g., diisopropyl sebacate, diisopropyl adipate, di-n-butyl phthalate), polyhydric alcohol esters of $C_6$–$C_{26}$ carboxylic acids (e.g., propylene glycol dicaprate/dicaprylate, propylene glycol isostearate); and mixtures thereof.

Even more preferred are branched-chain aliphatic fatty alcohols having from about 12–26 carbon atoms. Even more preferred is isocetyl alcohol, octyldecanol, octyldodecanol and undecylpentadecanol; and most preferred is octyldodecanol. Such preferred aliphatic fatty alcohols are particularly useful in combination with the volatile liquid silicone oils discussed herein to adjust the average solubility of the liquid base material.

3. Non-polar, Non-volatile Emollients

In addition to the liquids discussed above, the liquid base material may optionally include non-volatile, non-polar emollients which tend to improve product cosmetics. Typical non-volatile, non-polar emollients are disclosed, for example, in Cosmetics, Science, and Technology, Vol. 1, 27–104 edited by Balsam and Sagarin, 1972; U.S. Pat. Nos. 4,202,879 issued to Shelton on May 13, 1980; and 4,816,261 issued to Luebbe et al. on Mar. 28, 1989. The non-volatile oils useful in the present invention are essentially non-volatile polysiloxanes, paraffinic hydrocarbon oils, and mixtures thereof. The polysiloxanes useful in the present invention selected from the group consisting of polyalkylsiloxanes, polyarylsiloxanes, polyalkylarylsiloxanes, poly-ethersiloxane copolymers, and mixtures thereof. Examples of these include polydimethyl siloxanes having viscosities of from about 5 to about 100,000 centistokes at 25° C.

Among the preferred non-volatile silicone emollients useful in the present compositions are the polydimethyl siloxanes having viscosities from about 2 to about 400 centistokes at 25° C. Such polyalkylsiloxanes include the Viscasil series (sold by General Electric Company) and the Dow Corning 200 series (sold by Dow Corning Corp.). Polyalkylarylsiloxanes include polymethylphenyl siloxanes having viscosities of from about 15 to about 65 centistokes at 25° C. These are available, for example, as SF 1075 methyl-phenyl fluid (sold by General Electric Company) and 556 Cosmetic Grade Fluid (sold by Dow Corning Corp.). Useful polyethersiloxane copolymers include, for example, a polyoxyalkylene ether copolymer having a viscosity of about 1200 to 1500 centistokes at 25° C. Such a fluid is available as SF1066 organosilicone surfactant (sold by General Electric Company). Polysiloxane ethylene glycol ether copolymers are preferred copolymers for use in the present compositions.

Non-volatile paraffinic hydrocarbon oils useful in the present invention include mineral oils and certain branched-chain hydrocarbons. Examples of these fluids are disclosed in U.S. Pat. No. 5,019,375 issued to Tanner et al. on May 28, 1991. Preferred mineral oils have the following properties:

(1) viscosity from about 5 centistokes to about 70 centistokes at 40° C.;
(2) density between about 0.82 and 0.89 $g/cm^3$ at 25° C.;
(3) flash point between about 138° C. and about 216° C.; and
(4) carbon chain length between about 14 and about 40 carbon atoms.

Preferred branched chain hydrocarbon oils have the following properties:

(1) density between about 0.79 and about 0.89 $g/cm^3$ at 20° C.
(2) boiling point greater than about 250° C.; and
(3) flash point between about 110° C. and about 200° C.

Particularly preferred branched-chain hydrocarbons include Permethyl 103 A, which contains an average of about 24 carbon atoms; Permethyl 104A, which contains an average of about 68 carbon atoms; Permethyl 102A, which contains an average of about 20 carbon atoms; all of which may be purchased from Permethyl Corporation; and Ethylflo 364 which contains a mixture of 30 carbon atoms and 40 carbon atoms and may be purchased from Ethyl Corp.

C. Antiperspirant Active

The compositions of the present invention also contain an astringent antiperspirant active. These actives are used at levels from about 0.5% to about 60%, preferably from about 5% to about 35%, of the antiperspirant gel stick composition. This active may be incorporated either in solubilized or particulate form. These weight percentages are calculated on an anhydrous metal salt basis (exclusive of glycine, the salts of glycine, or other complexing agents). Such materials include, for example, many aluminum or zirconium astringent salts or complexes and are well known in the antiperspirant art.

Reduction in the amount of interaction between the antiperspirant active and the gelling agent results in better gel stick compositions. This interaction can be reduced by decreasing the surface area of the antiperspirant active; thereby reducing the interaction sites. Consequently, the antiperspirant active is preferably in particulate form wherein the surface area of the active is relatively low. The surface area of the antiperspirant active can be reduced by increasing the size and density of the active particles. Consequently, the particulate antiperspirant active preferably has a density which is preferably greater than about 0.7 g/cm$^3$ and an average particle size (as measured by a Coulter Multisizer 11 manufactured by Coulter Corporation, Haleah, Fla.) greater than about 10 microns; more preferably, greater than about 30 microns; and most preferably, greater than about 40 microns. Such preferred materials can be purchased from Westwood Chemical Company, Middletown, N.Y. under the trade name Westchlor ZR. Suitable antiperspirant active is disclosed, for example in U.S. Pat. No. 4,147,766 which issued on Apr. 3, 1979 to Kozischek.

Any aluminum astringent antiperspirant salt or aluminum and/or zirconium astringent complex can be employed herein. Salts useful as astringent antiperspirant salts or as components of astringent complexes include aluminum halides, aluminum hydroxy-halides, zirconyl oxyhalides, zirconyl hydroxy-halides, and mixtures of these materials.

Aluminum salts of this type include aluminum chloride and the aluminum hydroxyhalides having the general formula $Al_2(OH)_xQ_y \cdot XH_2O$ where Q is chlorine, bromine or iodine; where x is from about 2 to about 5, and x+y=about 6, and x and y do not need to be integers; and where X is from about 1 to about 6. Aluminum salts of this type can be prepared in the manner described more fully in U.S. Pat. Nos. 3,887,692 issued to Gilman on Jun. 3, 1975, and 3,904,741 issued to Jones and Rubino on Sep. 9, 1975.

The zirconium compounds which are useful in the present invention include both the zirconium oxy salts and zirconium hydroxy salts, also referred to as the zirconyl salts and zirconyl hydroxy salts. These compounds may be represented by the following general empirical formula:

$$ZrO(OH)_{2-nz}B_z$$

wherein z may vary from about 0.9 to about 2 and need not be an integer, n is the valence of B, 2-nz is greater than or equal to 0, and B may be selected from the group consisting of halides, nitrate, sulfamate, sulfate, and mixtures thereof. Although only zirconium compounds are exemplified in this specification, it will be understood that other Group IVB metal compounds, including hafnium, can be used in the present invention.

As with the basic aluminum compounds, it will be understood that the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxy group, varying from about 1.1 to only slightly greater than zero groups per molecule.

Several types of antiperspirant complexes utilizing the above antiperspirant salts are known in the art. For example, U.S. Pat. No. 3,792,068 issued to Luedders et al. on Feb. 12, 1974 discloses complexes of aluminum, zirconium and amino acids, such as glycine. Complexes such as those disclosed in the Luedders et al. patent and other similar complexes are commonly known as ZAG. ZAG complexes are chemically analyzable for the presence of aluminum, zirconium and chlorine. ZAG complexes useful herein are identified by the specification of both the molar ratio of aluminum to zirconium (hereinafter "Al:Zr" ratio) and the molar ratio of total metal to chlorine (hereinafter "Metal:Cl" ratio). ZAG complexes useful herein have an Al:Zr ratio of from about 1.67 to about 12.5 and a Metal:Cl ratio of from about 0.73 to about 1.93.

Preferred ZAG complexes are formed by
(A) co-dissolving in water
  (1) one part $Al_2(OH)_{6-m}Q_m$, wherein Q is an anion selected from the group consisting of chloride, bromide and iodide, and m is a number from about 0.8 to about 2.0;
  (2) x parts $ZrO(OH)_{2-a}Q_a \cdot nH_2O$, where Q is chloride, bromide or iodide; where a is from about 1 to about 2; where n is from about 1 to about 8; and where x has a value of from about 0.16 to about 1.2;
  (3) p parts neutral amino acid selected from the group consisting of glycine, dl-tryptophane, dl-b-phenylalanine, dl-valine, dl-methionine and b-alanine, and where p has a value of from about 0.06 to about 0.53;
(B) co-drying the resultant mixture to a friable solid; and.
(C) reducing the resultant dried inorganic-organic antiperspirant complex to particulate form.

A preferred aluminum compound for preparation of such ZAG type complexes is aluminum chlorhydroxide of the empirical formula $Al_2(OH)_5Cl \cdot 2H_2O$. Preferred zirconium compounds for preparation of such ZAG-type complexes are zirconyl hydroxychloride having the empirical formula $ZrO(OH)Cl \cdot 3H_2O$ and the zirconyl hydroxyhalides of the empirical formula $ZrO(OH)_{2-a}Cl_2 \cdot nH_2O$ wherein a is from about 1.5 to about 1.87, and n is from about 1 to about 7. The preferred amino acid for preparing such ZAG-type complexes is glycine of the formula $CH_2(NH_2)COOH$. Salts of such amino acids can also be employed in the antiperspirant complexes. See U.S. Pat. No. 4,017,599 issued to Rubino on Apr. 12, 1977.

A wide variety of other types of antiperspirant complexes are also known in the art. For example, U.S. Pat. No. 3,903,258 issued to Siegal on Sep. 2, 1975 discloses a zirconium aluminum complex prepared by reacting zirconyl chloride with aluminum hydroxide and aluminum chlorhydroxide. U.S. Pat. No. 3,979,510 issued to Rubino on Sep. 7, 1976 discloses an antiperspirant complex formed from certain aluminum compounds, certain zirconium compounds, and certain complex aluminum buffers. U.S. Pat. No. 3,981,896 issued to Pauling on Sep. 21, 1976 discloses an antiperspirant complex prepared from art aluminum polyol compound, a zirconium compound and an organic buffer. U.S. Pat. No. 3,970,748 issued to Mecca on Jul. 20, 1976 discloses an aluminum chlorhydroxy glycinate complex of the approximate general formula [Al$_2$(OH)$_4$Cl][H$_2$CNH$_2$COOH].

Of all the above types of antiperspirant actives, preferred compounds include the 5/6 basic aluminum salts of the empirical formula Al$_2$(OH)$_5$Cl.2H$_2$O; mixtures of AlCl$_3$.6H$_2$O and Al$_2$(OH)$_5$Cl. 2H$_2$O with aluminum chloride to aluminum hydroxychloride weight ratios of up to about 0.5; ZAG type complexes wherein the zirconium salt is ZrO(OH)Cl.3H$_2$O, the aluminum salt is Al$_2$(OH)$_5$Cl. 2H$_2$O or the aforementioned mixtures of AlCl$_3$.6H$_2$O and Al$_2$(OH)$_5$ Cl.2H$_2$O wherein the total metal to chloride molar ratio in the complex is less than about 1.25 and the Al:Zr molar ratio is about 3.3, and the amino acid is glycine; and ZAG-type complexes wherein the zirconium salt is ZrO(OH)$_{2-a}$Cl$_a$.nH$_2$O wherein a is from about 1.5 to about 1.87 and n is from about 1 to about 7, the aluminum salt is Al$_2$(OH)$_5$Cl.2H$_2$O, and the amino acid is glycine.

Solubilized antiperspirant actives which may be utilized in the present invention are also well known in the art. These materials utilize monohydric or polyhydric alcohols or water to solublize the antiperspirant active before it is incorporated into the product. The levels of these polar solvents is less than 25%, and preferably less than 15% of the composition. Examples of such actives are taught, for example, in U.S. Pat. No. 4,137,306 issued to Rubino on Jan. 30, 1979; U.S. patent application Ser. No. 370,559, Smith and Ward, filed Jun. 23, 1989; and European Patent Application 0295070 which published Dec. 14, 1988.

D. Optional Ingredients:

Antiperspirant gel stick compositions of the present invention may contain optional components which act as additional active or modify the physical characteristics of the composition or the components making up said compositions. Such components are well known in the art. A non-limiting group of these optional components include colorants, perfumes, thickeners, distributing agents, emulsifiers, bacteriostats, fungistats, and mixtures thereof. Optional components useful herein are described in the following references: U.S. Pat. No. 4,049,792 issued to Elsnau on Sep. 20, 1977; Canadian Patent 1,164,347 which issued to Beckmeyer et al. on Mar. 27, 1984; European Patent Application 117,070 which published on Aug. 29, 1984; and Geria, "Formulation of Stick Antiperspirants and Deodorants", *Cosmetics and Toiletries*, 99: 55–60 (1984).

Emulsifiers are particularly useful in the present invention. These emulsifiers include non-ionic surfactants useful for forming water-in-oil emulsions. The level of emulsifiers used in the present invention is typically less than about 10%, preferably less than about 5%. Examples of these emulsifiers include polyoxyethylene ethers of fatty alcohols, and polyoxyethylene-polysiloxane copolymers. Such emulsifiers are disclosed by EPO Application 373,424 Raleigh et al., and U.S. Ser. No. 530,671, Cedeno et al., filed Jul. 2, 1991.

Thickeners are also useful in the presently invention. Their selection and the level they are used at should be so as not to significantly affect the aesthetics of the gel composition. Typical levels of thickeners are at levels of less than about 5%. Examples of said thickeners are disclosed in U.S. Pat. No. 4,985,238, Tanner et al., issued Jan. 15, 1991; herein incorporated by reference.

These thickeners include wax-like materials such as beeswax, cerasin, hydrogenated castor oil, synthetic waxes such as Fisher Tropsch waxes, microcrystalline waxes, polyethylene waxes, and mixtures thereof.

Particulate and filler materials may also be included in the present compositions. These materials are typically used at levels from about 0.5% to about 5%, preferably not more than 3%. Such materials are disclosed in U.S. Pat. No. 5,019,375, Tanner et al., issued May 28, 1991. Suitable filler materials include collodial silica (such as Cab-O-Sil, sold by Cabot Corp), clays (such as bentonite), hydrophobic (quaternized) clays, silica/alumina thickeners, silicate powders such as talc, alumina silicate, and magnesium silicate, modified corn starches, metallic stearates, and mixtures thereof. The use of such fillers as stabilizing agents in cosmetic sticks is disclosed in U.S. Pat. No. 4,126,679, Davy et al., issued Nov. 21, 1987, incorporated by reference. Examples of other particulate materials include particulate hydrophilic polymers such as cellulose ether polymers, modified starches, polyamides, and polypeptides.

A wash-off agent may be utilized to improve the ease with which the ingredients—particularly the gelling agent and the non-polar, non-volatile oils—may be washed off. The wash-off agent is highly preferably a non-liquid. The wash-off agent is typically in the antiperspirant stick composition in an amount from about 0.1% to about 10%.

Typical wash-off agents are non-liquids selected from the group consisting of polyoxyethylene ethers having the formula R$_1$(OCH$_2$CH$_2$)$_n$OH; polyoxyethylene esters having the formula R$_1$CO(OCH$_2$CH$_2$)$_n$OH; polyoxyethylene glyceryl esters having the formula (R$_1$COO)CH$_2$CH(OH)CH$_2$(OCH$_2$CH$_2$)$_n$OH or having the formula HOCH$_2$CH(OOCR$_1$)CH$_2$(OCH$_2$CH$_2$)$_n$OH; and polyoxyethylene glyceryl diesters having the formula R$_1$COOCH$_2$CH(OOCR$_2$)CH$_2$(OCH$_2$CH$_2$)$_n$OH—preferably, the polyoxyethylene ethers—wherein: R$_1$ and R$_2$ are the same or different alkyl, alkenyl, or aromatic hydrocarbon radical which may be substituted or unsubstituted—preferably an alkyl radical—having from about 4 to about 22 carbon atoms; and n is from about 2 to about 80.

Preferred examples of such wash-off agents include: ceteth-2 through ceteth-30, steareth-2 through steareth-30, ceteareth-2 through ceteareth-30, PEG-2 stearate through PEG-30 stearate, PEG-12 isostearate, PEG-16 hydrogenated castor oil, PEG-40 hydrogenated castor oil, and PEG-20 glyceryl stearate; more preferably, ceteareth-20, steareth-21, PEG-20 stearate, and PEG-16 hydrogenated castor oil; and most preferably, ceteareth-20.

METHODS OF MANUFACTURE

The present invention may be made by using any of the typical methods known to those skilled in the art, and disclosed in *Gels and Sticks Formulary*, 99 Cosmetics & Toiletries 77–84, 1984; herein incorporated by reference. Methods found particularly useful follow below:

Combine the gelling agent and the liquid base material into a vessel equipped with a heat source. Heat the mixture to between about 80° C. and about 130° C. with stirring, until the mixture forms a homogeneous, molten solution. Preferably, the homogeneous, molten solution is allowed to cool to a mixing temperature; typically between about 65° C. and 120° C. Alternatively, the mixture may simply be heated to the mixing temperature until the mixture forms a homogeneous, molten solution. This alternative method, however, typically takes longer than simply overheating and then cooling. Add the antiperspirant active and other ingredients, such as fragrances and colors, into the homogeneous, molten solution in the above vessel with stirring. Allow the mixture to cool untill it begins thichening and then pour the mixture into containers allowing them to cool to ambient temperature. Although not preferred, the antiperspirant active may alternatively be added along with the gelling agent and the liquid base material in the first step.

METHODS FOR USE

The present invention provides methods for preventing perspiration and malodor associated with human perspiration. These methods comprise applying to the skin of a human a safe and effective amount of the antiperspirant gel of the present invention. The term "a safe and effective amount" as used herein, is an amount which is effective in eliminating or substantially reducing malodor associated with human underarm perspiration while being safe for human use at a reasonable risk/benefit ratio. Typically, the safe and effective amount used is from about 0.1 gram per axilla to about 1.0 gram per axilla.

EXAMPLES

The following examples further describe and demonstrate embodiments within the scope of the present invention. These examples are solely for the purpose of illustration and are not to be construed as limitations of the present invention as many variations are possible without departing from the spirit or scope thereof.

The levels of the components in the examples below are expressed by total weight of the composition.

|  | I | II | III | IV | V | VI | VII | VIII |
|---|---|---|---|---|---|---|---|---|
| N-Lauroyl-L-glutamic acid-di-n-butyl amide[1] | 4 | 5 | 1 | 3 | 2 | 2 | 2 | 1 |
| 12-hydroxystearic acid | 2 | 5 | 5 | 6 | 7 | 3 | 6 | 12 |
| Cyclomethicone D-5[2] |  | 40 | 49 | 39 | 43 | 40 | 43 | 46 |
| Polyphenylmethylsiloxane[3] |  |  |  | 3 |  |  | 5 |  |
| Light mineral oil[4] | 23 |  |  |  |  |  |  |  |
| Panalane-L-14E[5] |  | 15 | 10 | 11 |  |  |  |  |
| Isopropyl Myristate |  | 15 | 15 | 16 |  |  | 11 |  |
| Isopropyl Alcohol |  |  |  |  | 18 |  |  |  |
| Captex 200[6] |  |  |  |  |  | 15 |  |  |
| C12–C15 Alcohols Benzoate[7] |  |  |  |  |  |  | 8 |  |
| PPG-3 Myristyl Ether |  |  |  |  |  |  |  | 26 |
| Diisopropyl Sebacate[8] | 43 |  |  |  |  |  |  |  |
| Aluminum Zirconium Trichlorhydrex Gly[9] | 25 | 20 | 20 | 20 |  | 40 | 25 |  |
| Aluminum Chlorohydrate[10] |  |  |  |  | 30 |  |  | 10 |
| Talc | 3 |  |  | 2 |  |  |  | 5 |
|  | 100 | 100 | 100 | 100 | 100 | 100 | 100 | 100 |

[1]GP-1 supplied by Ajinomoto, Inc.
[2]Dow Corning 245 Fluid-cyclic polydimethylsiloxane
[3]Dow Corning 556 Fluid
[4]Benol White Mneral OH supplied by Witco Chemical Corp
[5]Polyisobutene supplied by Amoco Chemical Company
[6]Propylene glycol dicaprate/dicaprylate supplied by Capital City Products
[7]Finsolv TN supplied by Finetex
[8]Schercemol DIS supplied by Scher Cherfficals Inc.
[9]Supplied by Westwood Chemical Co.
[10]Westchlor DM200 supplied by Westwood Chemical Co.

|  | IX | X | XI | XII | XIII | XIV | XV | XVI | XVII | XVIII |
|---|---|---|---|---|---|---|---|---|---|---|
| N-Lauroyl-L-glutamic acid-di-n-butyl amide[1] | 2 | 2 | 2 | 2 | 2 | 2 | 2 | 2 | 2 | 2 |
| 12-hydroxystearic acid | 6 | 6 | 6 | 6 | 6 | 6 | 6 | 6 | 6 | 6 |
| Cyclomethicone D-4[2] | 58.5 |  | 26.5 |  | 57 | 53.5 | 55 | 53 |  |  |
| Cyclomethicone D-5[3] |  | 57.5 |  | 52.5 |  |  |  |  | 49 | 48.75 |
| PPG-3-myristyl ether |  |  |  |  |  | 12 |  |  |  |  |
| PPG-5-butyl ether |  |  |  |  |  |  | 10.5 |  |  |  |
| PPG-10-cetyl ether |  |  |  |  |  |  |  | 12.5 |  |  |
| Isocetyl alcohol | 7 | 8 | 13 |  |  |  |  |  |  |  |
| Isostearyl alcohol |  |  |  | 13 |  |  |  |  |  |  |
| Octyldodecanol |  |  |  |  | 8.5 |  |  |  | 14 | 14 |
| Polydecene[4] |  |  | 26 |  |  |  |  |  |  |  |
| Ceteareth-20 |  |  |  |  |  |  |  |  | 2.5 | 2.5 |
| Dipropyleneglycol |  |  |  |  |  |  |  |  |  | 0.25 |
| C20–40 alcohols[5] |  |  |  |  |  |  |  |  | 0.5 | 0.5 |
| C40–60 alcohols[6] | 0.5 | 0.5 | 0.5 | 0.5 | 0.5 | 0.5 | 0.5 | 0.5 |  |  |
| Aluminum Zirconium Trichlorhydrex Gly[7] | 26 | 26 | 26 | 26 | 26 | 26 | 26 | 26 | 26 | 26 |
|  | 100 | 100 | 100 | 100 | 100 | 100 | 100 | 100 | 100 | 100 |

[1]GP-1 supplied by Ajinomoto, Inc.
[2]Dow Corning 245 Fluid - cyclic polydimethylsiloxane
[3]Dow Corning 244 Fluid - cyclic polydimethylsdoxane
[4]Ethylflo 364 supplied by Ethyl Corp.
[5]Untin 425 supplied by Petrolite
[6]Untin 700 supplied by Petrolite
[7]Supplied by Westwood Chemical Co.

|  | XIX | XX | XXI | XXII | XXIII | XXIV | XXV |
|---|---|---|---|---|---|---|---|
| N-Stearyl-L-glutamic acid-di-n-hexyl amide[1] | 2 | 2 |  |  |  |  |  |

| | | | | | | | |
|---|---|---|---|---|---|---|---|
| -continued | | | | | | | |
| N-Lauroyl-L-glutamic acid-di-n-octyl amide[1] | | 2 | 2 | | | | |
| N-Lauroyl-L-glutamic acid-di-n-decyl amide[1] | | | | 2 | | | |
| N-Stearyl-L-glutamic acid-di-n-decyl amide[1] | | | | | 2 | | |
| N-Lauroyl-L-glutamic acid-di-n-stearyl amide[1] | | | | | | | 2 |
| 12-hydroxystearic acid | | | 6 | 6 | 6 | 6 | 6 |
| Isopropyl amide of 12-hydroxystearic acid[1] | 6 | 6 | | | | | |
| Cyclomethicone D-5[2] | 40.5 | 49 | 40.5 | 49 | 40.5 | 40.5 | 40.5 |
| C12–15 Alcohols Benzoate[3] | 25 | | 25 | | 25 | 25 | 25 |
| Octyldodecanol | | 14 | | 14 | | | |
| Ceteareth-20 | | 2.5 | | 2.5 | | | |
| C40–60 alcohols[4] | 0.5 | 0.5 | 0.5 | 0.5 | 0.5 | 0.5 | 0.5 |
| Aluminum Zirconium Trichlorhydrex Gly[5] | 26 | 26 | 26 | 26 | 26 | 26 | 26 |
| | 100 | 100 | 100 | 100 | 100 | 100 | 100 |

[1]Supplied by Starks Chemical Co.
[2]Dow Corning 245 Fluid - cyclic polydimethylsiloxane
[3]Finsolv TN supplied by Finetex
[4]Unilin 700 supplied by Petrolite
[5]Supplied by Westwood Chemical Co.

The antiperspirant gel stick compositions are prepared by combining the gelling agent, the Non-polar, volatile oil, the relatively polar, non-volatile co-solvent and other components of the liquid base material. This combination of components is heated to a temperature from about 80° C. to about 130° C. to form a clear, homogeneous solution. Once clear, the solution is cooled to a mixing temperature of from about 65° C. and about 120° C.; at which time the antiperspirant active (and other optional components such as filler powders or perfumes) is added. The active is mixed thoroughly into the composition and the mixture is poured into containers. Upon cooling a stable antiperspirant gel stick is obtained.

Although particular examples of antiperspirant gel stick compositions of the present invention has been described, modifications may be made without departing from the spirit and scope of the present invention. Accordingly, the present invention comprises all embodiments within the scope of the appended claims.

All documents referred to herein, including all patents, all patent applications and all articles, are hereby incorporated herein by reference in their entirety.

All percentages herein are by weight of the total composition and all ratios are weight ratios unless otherwise indicated. All percentages, ratios, and levels of ingredients referred to herein are based upon the actual amount of the ingredient, and do not include solvents, fillers, or other materials with which the ingredient may be combined when supplied commercially, unless otherwise indicated.

All numerical ranges specified herein, hereby expressly include each and every numerical value therebetween, as if it were expressly written therein.

We claim:

1. An antiperspirant gel stick composition comprising:
   a. from about 0.5% to about 60%, by weight of an antiperspirant active;
   b. from about 1% to about 15% of a gelling agent including: a primary gellant selected from the group consisting of 12-hydroxystearic acid, esters of 12-hydroxystearic acid, amides of 12-hydroxystearic acid, and mixtures thereof, said primary gellant having the formula:

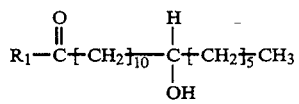

wherein $R_1$ is $OR_2$ or $NR_2R_3$; and $R_2$ and $R_3$ are the same or different and are hydrogen, or an alkyl, aryl, or arylalkyl radical which are branched, linear or cyclic and have from about 1 to about 22 carbon atoms; and a secondary gellant selected from the group consisting of n-acyl glutamic acid amides, n-acyl glutamic acid esters, and mixtures thereof having the following formula:

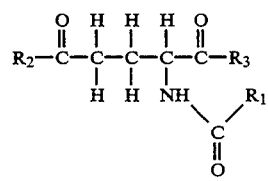

wherein $R_1$ is an alkyl, aryl, arylalkyl radical is branched, linear or cyclic and has from about 1 to about 6 carbon atoms; and $R_2$ and $R_3$ are the same or different alkyl, aryl, arylalkyl ester radical or alkyl, aryl, arylalkyl amide radical, in which the moiety is branched, linear or cyclic and has from about 1 to about 26 carbon atoms, said composition having a ratio of primary to secondary gellant of from about 1:2 to about 20:1; and c. from about 10% to about 95% of a liquid base material capable of solubilizing the gelling agent, whereby a heated solution of said gelling agent and liquid base material forms a stick when cooled to ambient temperature.

2. An antiperspirant gel stick composition according to claim 1, wherein the n-acyl amino acid derivative is selected from the group consisting of n-acyl glutamic acid amides and n-acyl glutamic acid esters corresponding to the following formula:

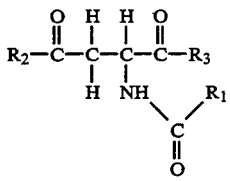

wherein $R_1$ is an alkyl, aryl, arylalkyl radical is branched, linear or cyclic and has from about 6 to about 22 carbon atoms; and $R_2$ and $R_3$ are the same or different alkyl, aryl, arylalkyl ester radical or alkyl, aryl, arylalkyl amide radical, in which the moeity is branched, linear or cyclic and has from about 2 to about 20 carbon atoms.

3. An antiperspirant gel stick composition as in claim 1, wherein said liquid base material has an average solubility parameter of from about 6 to about 10.

4. An antiperspirant gel stick composition comprising:
   a. from about 0.5% to about 60%, by weight, of an antiperspirant active;
   b. from about 1% to about 15% of a gelling agent including: a primary gellant selected from the group consisting of 12-hydroxystearic acid, esters of 12-hydroxystearic acid, amides of 12-hydroxystearic acid, and mixtures thereof, said primary gellant having the formula:

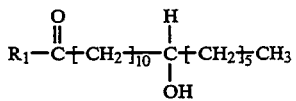

wherein $R_1$ is $OR_2$ or $NR_2R_3$; and $R_2$ and $R_3$ are the same or different and are hydrogen, or an alkyl, aryl, or arylalkyl radical which are branched, linear or cyclic and have from about 1 to about 22 carbon atoms; and a secondary gellant selected from the group consisting of n-acyl glutamic acid amides, n-acyl glutamic acid esters, and mixtures thereof having the following formula:

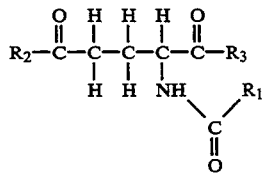

wherein $R_1$ is an alkyl, aryl, arylalkyl radical is branched, linear or cyclic and has from about 6 to about 22 carbon atoms; and $R_2$ and $R_3$ are the same or different alkyl, aryl, arylalkyl ester radical or alkyl, aryl, arylalkyl amide radical, in which the moiety is branched, linear or cyclic and has from about 2 to about 20 carbon atoms, and said composition having a ratio of primary to secondary gellant of from about 1:2 to about 20:1; and
   c. from about 10% to about 95% of a liquid base material said liquid base material comprising a non-polar, volatile oil and a relatively polar, non-volatile co-solvent soluble in the non-polar, volatile oil and capable of solubilizing the primary gellant, the secondary gellant, or a mixture thereof.

5. An antiperspirant gel stick composition as in claim 4, wherein said liquid base material has an average solubility parameter of from about 6 to about 10.

6. An antiperspirant gel stick composition according to claim 5, wherein the non-polar, volatile silicone oil is selected from the group consisting of cyclic volatile silicones corresponding to the formula:

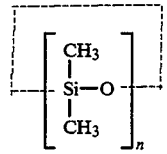

wherein n is from about 3 to about 7; linear volatile silicones corresponding to the formula:

$$(CH_3)_3Si-O-[Si(CH_3)_2O]_m-Si(CH_3)_3$$

wherein m is from about 1 to about 7, and mixtures thereof.

7. An antiperspirant gel stick composition according to claim 5, wherein the relatively polar co-solvent is selected from the group consisting of fatty alcohols having from about 12–26 carbon atoms; fatty acids having from about 12–26 carbon atoms; esters of monobasic carboxylic acids and alcohols having from about 14–30 carbon atoms; esters of dibasic carboxylic acids and alcohols having from about 10–30 carbon atoms; esters of polyhydric alcohols and carboxylic acids having from about 5–26 carbon atoms; ethoxylated, propoxylated, and mixtures of ethoxylated and propoxylated ethers of fatty alcohols with from about 12–26 carbon atoms and a degree of ethoxylation and propoxylation of below about 50; and mixtures thereof.

8. An antiperspirant gel stick composition according to claim 6 wherein the relatively polar co-solvent is selected from the group consisting of fatty alcohols having from about 12–26 carbon atoms; fatty acids having from about 12–26 carbon atoms; esters of monobasic carboxylic acids and alcohols having from about 14–30 carbon atoms; esters of dibasic carboxylic acids and alcohols having from about 10–30 carbon atoms; esters of polyhydric alcohols and carboxylic acids having from about 5–26 carbon atoms; ethoxylated, propoxylated, and mixtures of ethoxylated and propoxylated ethers of fatty alcohols with from about 12–26 carbon atoms and a degree of ethoxylation and propoxylation of below about 50; and mixtures thereof.

9. An antiperspirant gel stick composition according to claim 4, wherein the antiperspirant active has an average particle size greater than about 30 microns and a density greater than about 0.7 grams per cubic centimeter.

10. An antiperspirant gel stick composition according to claim 8, wherein the antiperspirant active has an average particle size greater than about 30 microns and a density greater than about 0.7 grams per cubic centimeter.

11. An antiperspirant gel stick composition comprising:
   a. from about 5% to about 35% of an antiperspirant active;
   b. from about 3% to about 12% of a gelling agent including; a primary gellant selected from the group consisting of 12-hydroxystearic acid, esters of 12-hydroxystearic acid, amides of 12-hydroxystearic acid, and mixtures thereof said primary gellant having the formula:

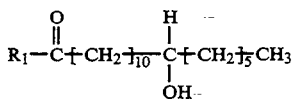

wherein $R_1$ is $OR_2$ or $NR_2R_3$; and $R_2$ and $R_3$ are the same or different and are hydrogen, or an alkyl, aryl, or arylalkyl radical which are branched, linear or cyclic and have from about 1 to about 22 carbon atoms; and a secondary gellant selected from the group consisting of n-acyl glutamic acid amides, n-acyl glutamic acid esters, and mixtures thereof having the following formula:

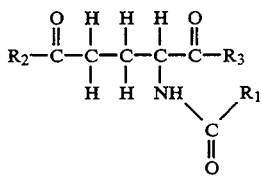

wherein $R_1$ is an alkyl, aryl, arylalkyl radical is branched, linear or cyclic and has from about 6 to about 22 carbon atoms; and $R_2$ and $R_3$ are the same or different alkyl, aryl, arylalkyl ester radical or alkyl, aryl, arylalkyl amide radical, in which the moiety is branched, linear or cyclic and has from about 2 to about 20 carbon atoms; wherein the primary gellant:secondary gellant ratio is from about 1:1 to about 10:1; and c. from about 30% to about 80% of a liquid base material including from about 25% to about 60% of a non-polar, volatile oil and from about 5% to about 25% of a relatively polar, non-volatile co-solvent soluble in the non-polar, volatile oil and capable of solubilizing the primary gellant, the secondary gellant, or a mixture thereof.

12. An antiperspirant gel stick composition according to claim 11, wherein the non-polar, volatile silicone oil is selected from the group consisting of cyclic volatile silicones corresponding to the formula:

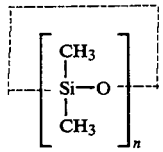

wherein n is from about 3 to about 7; linear volatile silicones corresponding to the formula:

$(CH_3)_3Si—O—[Si(CH_3)_2O]_m—Si(CH_3)_3$ wherein m is from about 1 to about 7, and mixtures thereof.

13. An antiperspirant gel stick composition according to claim 12; wherein the relatively polar co-solvent is selected from the group consisting of fatty alcohols having from about 12–26 carbon atoms; fatty acids having from about 12–26 carbon atoms; esters of monobasic carboxylic acids and alcohols having from about 14–30 carbon atoms; esters of dibasic carboxylic acids and alcohols having from about 10–30 carbon atoms; esters of polyhydric alcohols and carboxylic acids having from about 5–26 carbon atoms; ethoxylated, propoxylated, and mixtures of ethoxylated and propoxylated ethers of fatty alcohols with from about 12–26 carbon atoms and a degree of ethoxylation and propoxylation of below about 50; and mixtures thereof.

14. An antiperspirant gel stick composition comprising:

a. from about 5% to about 35% of an antiperspirant active;

b. from about 3% to about 12% of a gelling agent including; a primary gellant selected from the group consisting of 12-hydroxystearic acid, esters of 12-hydroxystearic acid, amides of 12-hydroxystearic acid, and mixtures thereof said primary gellant having the formula:

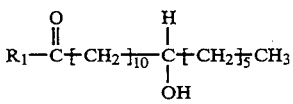

wherein $R_1$ is $OR_2$ or $NR_2R_3$; and $R_2$ and $R_3$ are the same or different and are hydrogen, or an alkyl, aryl, or arylalkyl radical which are branched, linear or cyclic and have from about 1 to about 22 carbon atoms; and a secondary gellant selected from the group consisting of n-acyl glutamic acid amides, n-acyl glutamic acid esters, and mixtures thereof having the following formula:

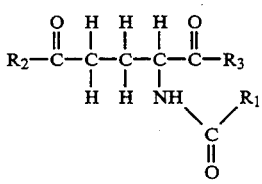

wherein $R_1$ is an alkyl, aryl, arylalkyl radical is branched, linear or cyclic and has from about 6 to about 22 carbon atoms; and $R_2$ and $R_3$ are the same or different alkyl, aryl, arylalkyl ester radical or alkyl, aryl, arylalkyl amide radical, in which the moiety is branched, linear or cyclic and has from about 2 to about 20 carbon atoms; wherein the primary gellant:secondary gellant ratio is from about 1:1 to about 10:1; and c. from about 45% to about 80% of a liquid base material including from about 40% to about 60% of a non-polar, volatile oil wherein the non-polar, volatile silicone oil is selected from the group consisting of cyclic volatile silicones corresponding to the formula:

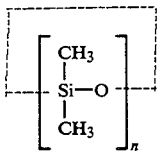

wherein n is from about 3 to about 7, linear volatile silicones corresponding to the formula:

$(CH_3)_3Si—O—[Si(CH_3)_2O]_m—Si(CH_3)_3$ wherein m is from about 1 to about 7, and mixtures thereof; and from about 5% to about 25% of a relatively polar, non-volatile co-solvent selected from the group consisting of branched-chain aliphatic fatty alcohols having from about 12–26 carbon atoms; the relatively polar, non-volatile co-solvent is soluble in the non-polar, volatile oil and capable of solubilizing the primary gellant, the secondary gellant, or a mixture thereof;

wherein a heated solution of the gelling agent and the liquid base material remains in solution such that the antiperspirant active can be uniformly mixed into the composition at a temperature less than about 120° C.

15. An antiperspirant gel stick composition as in claim 14, wherein said liquid base material has an average solubility parameter of from about 6 to about 10.

16. An antiperspirant gel stick composititon according to claim 14, wherein the primary gellant is selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, and mixtures thereof.

17. An antiperspirant gel stick composition according to claim 14, wherein said secondary gellant is selected from the group consisting of N-lauroyl-glutamic acid diethyl amide, N-lauroyl-glutamic acid dibutyl amide, N-lauroyl-glutamic acid dihexyl amide, N-lauroyl-glutamic acid dioctyl amide, N-lauroyl-glutamic acid didecyl amide, N-lauroyl-glutamic acid didodecyl amide, N-lauroyl-glutamic acid ditetradecyl amide, N-lauroyl-glutamic acid dihexadecyl amide, N-lauroyl-glutamic acid distearyl amide, N-stearoyl-glutamic acid dibutyl amide, N-stearoyl-glutamic acid dihexyl amide, N-stearoyl-glutamic acid diheptyl amide, N-stearoyl-glutamic acid dioctyl amide, N-stearoyl-glutamic acid didecyl amide, N-stearoyl-glutamic acid didodecyl amide, N-stearoyl-glutamic acid ditetradecyl amide, N-stearoyl-glutamic acid dihexadecyl amide, N-stearoyl-glutamic acid distearyl amide and mixtures thereof.

18. An antiperspirant gel stick composition according to claim 17, wherein said secondary gellant is selected from the group consisting of N-lauroyl-glutamic acid diethyl amide, N-lauroyl-glutamic acid dibutyl amide, N-lauroyl-glutamic acid dihexyl amide, N-lauroyl-glutamic acid dioctyl amide, N-lauroyl-glutamic acid didecyl amide, N-lauroyl-glutamic acid didodecyl amide, N-lauroyl-glutamic acid ditetradecyl amide, N-lauroyl-glutamic acid dihexadecyl amide, N-lauroyl-glutamic acid distearyl amide, N-stearoyl-glutamic acid dibutyl amide, N-stearoyl-glutamic acid dihexyl amide, N-stearoyl-glutamic acid diheptyl amide, N-stearoyl-glutamic acid dioctyl amide, N-stearoyl-glutamic acid didecyl amide, N-stearoyl-glutamic acid didodecyl amide, N-stearoyl-glutamic acid ditetradecyl amide, N-stearoyl-glutamic acid dihexadecyl amide, N-stearoyl-glutamic acid distearyl amide and mixtures thereof.

19. An antiperspirant gel stick composition according to claim 14, wherein the antiperspirant active has an average particle size greater than about 30 microns and a density greater than about 0.7 grams per cubic centimeter.

20. An antiperspirant gel stick composition according to claim 18, wherein the antiperspirant active has an average particle size greater than about 30 microns and a density greater than about 0.7 grams per cubic centimeter.

21. An antiperspirant gel stick composition according to claim 17, wherein said secondary gellant is selected from the group consisting of n-lauroyl-glutamic acid dibutyl amide, n-stearyl-glutamic acid dihexyl amide, and mixtures thereof.

22. An antiperspirant gel stick composition according to claim 18, wherein said secondary gellant is selected from the group consisting of n-lauroyl-glutamic acid dibutyl amide, n-stearyl-glutamic acid dihexyl amide, and mixtures thereof.

23. A method for controlling perspiration and malodor comprising applying an effective amount to the skin of a human of a composition comprising:
   a. from about 0.5% to about 60%, by weight of an antiperspirant active;
   b. from about 1% to about 15% of a gelling agent including: a primary gellant selected from the group consisting of 12-hydroxystearic acid, esters of 12-hydroxystearic acid, amides of 12-hydroxystearic acid, and mixtures thereof, said primary gellant having the formula:

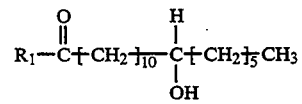

wherein $R_1$ is $OR_2$ or $NR_2R_3$; and $R_2$ and $R_3$ are the same or different and are hydrogen, or an alkyl, aryl, or arylalkyl radical which are branched, linear or cyclic and have from about 1 to about 22 carbon atoms; and a secondary gellant selected from the group consisting of n-acyl glutamic acid amides, n-acyl glutamic acid esters, and mixtures thereof having the following formula:

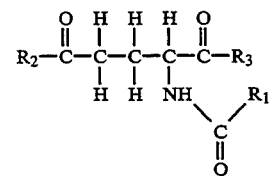

wherein $R_1$ is an alkyl, aryl, arylalkyl radical is branched, linear or cyclic and has from about 1 to about 6 carbon atoms; and $R_2$ and $R_3$ are the same or different alkyl, aryl, arylalkyl ester radical or alkyl, aryl, arylalkyl amide radical, in which the moiety is branched, linear or cyclic and has from about 1 to about 26 carbon atoms, said composition having a ratio of primary to secondary gellant of from about 1:2 to about 20:1; and
   c. from about 10% to about 95% of a liquid base material capable of solubilizing the gelling agent, whereby a heated solution of said gelling agent and liquid base material forms a stick when cooled to ambient temperature.

24. A method for controlling malodor comprising applying an effective amount to the skin of a human of a composition comprising:
   a. from about 0.5% to about 60%, by weight of an antiperspirant active;
   b. from about 1% to about 15% of a gelling agent including: a primary gellant selected from the group consisting of 12-hydroxystearic acid, esters of 12-hydroxystearic acid, amides of 12-hydroxystearic acid, and mixtures thereof, said primary gellant having the formula:

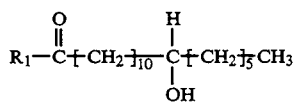

wherein $R_1$ is $OR_2$ or $NR_2R_3$; and $R_2$ and $R_3$ are the same or different and are hydrogen, or an alkyl, aryl, or arylalkyl radical which are branched, linear or cyclic and have from about 1 to about 22 carbon atoms; and a secondary gellant selected n-acyl amine acid amide derivatives; n-acyl glutamic acid amides, n-acyl glutamic acid esters, and mixtures thereof having the following formula:

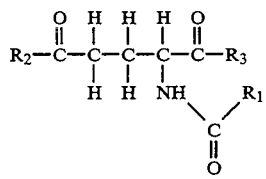

wherein $R_1$ is an alkyl, aryl, arylalkyl radical is branched, linear or cyclic and has from about 1 to about 6 carbon atoms; and $R_2$ and $R_3$ are the same or different alkyl, aryl, arylalkyl ester radical or alkyl, aryl, arylalkyl amide radical, in which the moiety is branched, linear or cyclic and has from about 1 to about 26 carbon atoms, said composition having a ratio of primary to secondary gellant of from about 1:2 to about 20:1; and
   c. from about 10% to about 95% of a liquid base; material capable of solubilizing the gelling agent, whereby a heated solution of said gelling agent and liquid base material forms a stick when cooled to ambient temperature.

* * * * *

UNITED STATES PATENT AND TRADEMARK OFFICE
CERTIFICATE OF CORRECTION

PATENT NO. : 5,429,816

DATED : July 4, 1995

INVENTOR(S) : Hofrichter et al.

It is certified that error appears in the above-indentified patent and that said Letters Patent is hereby corrected as shown below:

Column 2, line 51 "ing; of n-acyl" should read --ing of n-acyl--.

Column 3, line 39 "the galling agent" should read --the gelling agent--.

Column 5, line 11 "As o used" should read --As used--.

Column 11, line 1 "from art aluminum" should read --from an aluminum--.

Column 13, Examples I-VIII, Footnote 4 "White Mneral OH" should read --White Mineral Oil--.

Column 13, Examples I-VIII, Footnote 8 "Scher Cherfficals" should read --Scher Chemicals--.

Examples IX-XVIII, Footnote 3 "polydimethylsdoxane" should read --polydimethylsiloxane--.

Examples IX-XVIII, Footnote 5 "Untin 425" should read --Unilin 425--.

Examples IX-XVIII, Footnote 6 "Untin 700" should read --Unilin 700--.

UNITED STATES PATENT AND TRADEMARK OFFICE
CERTIFICATE OF CORRECTION

PATENT NO. : 5,429,816

DATED : July 4, 1995

INVENTOR(S) : Hofrichter et al.

Page 2 of 2

It is certified that error appears in the above-indentified patent and that said Letters Patent is hereby corrected as shown below:

Column 16, line 52 "and $R_3$are" should read --and $R_3$ are--.

Column 18, line 5 "claim 5" should read --claim 4--.

Column 18, line 25 "claim 5" should read --claim 4--.

Column 23, line 26 "n-acyl amine acid" should read --n-acyl amino acid--.

Column 24, line 21 "liquid base;" should read --liquid base--.

Signed and Sealed this

Tenth Day of December, 1996

Attest:

Attesting Officer

BRUCE LEHMAN

Commissioner of Patents and Trademarks